US010489963B2

(12) United States Patent
Benner

(10) Patent No.: US 10,489,963 B2
(45) Date of Patent: Nov. 26, 2019

(54) METHOD AND COMPUTER FOR VISUALIZATION OF FIBERS IN MEDICAL IMAGES

(71) Applicant: Siemens Healthcare GmbH, Erlangen (DE)

(72) Inventor: Thomas Benner, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/002,028

(22) Filed: Jun. 7, 2018

(65) Prior Publication Data
US 2018/0357815 A1 Dec. 13, 2018

(30) Foreign Application Priority Data
Jun. 7, 2017 (DE) .................. 10 2017 209 542

(51) Int. Cl.
*G06T 11/00* (2006.01)
*G16H 30/40* (2018.01)
(Continued)

(52) U.S. Cl.
CPC ............ *G06T 15/08* (2013.01); *A61B 5/0042* (2013.01); *A61B 5/044* (2013.01); *A61B 5/055* (2013.01); *A61B 5/4887* (2013.01); *G06T 11/008* (2013.01); *G09G 3/002* (2013.01); *G16H 30/40* (2018.01); *G16H 40/63* (2018.01);
(Continued)

(58) Field of Classification Search
CPC ... G06T 15/08; G06T 11/008; G06T 2200/04; G06T 2207/30016; G06T 2207/10088; G06T 2207/10092; G06T 2207/30004; G06T 2207/30048; G06T 2207/10072; G16H 30/40; G16H 40/63; A61B 5/055; A61B 5/0042; A61B 5/0044;
(Continued)

(56) References Cited

U.S. PATENT DOCUMENTS 6,642,716 B1 11/2003 Hoogenraad et al.
2006/0241897 A1 10/2006 Hoogenraad et al.
(Continued)

FOREIGN PATENT DOCUMENTS

DE 102013213010 B3 10/2014

*Primary Examiner* — Ke Xiao
*Assistant Examiner* — Andrew Shin
(74) *Attorney, Agent, or Firm* — Schiff Hardin LLP

(57) ABSTRACT

In a method for visualization of information from first and second 3D datasets representing directional information of a subject, wherein some voxels are combined along their respective directional information into multiple fibers, a first item of anatomical information, visible from a first viewing position on a fiber, is determined from the first 3D dataset, and is projected onto a first projection surface at a display dependent on the first viewing position. Upon detected movement away from the first viewing position, a guided movement along the fiber is determined, which is restricted to movement along one fiber. A second viewing position is determined in the subject relative to the selected fiber dependent on the guided movement, and a second item of anatomical information is determined from the first 3D dataset, which is visible from the second viewing position, and is projected onto a second projection surface at the display.

11 Claims, 3 Drawing Sheets

(51) Int. Cl.
*G06F 3/0484* (2013.01)
*G06T 15/08* (2011.01)
*A61B 5/055* (2006.01)
*G09G 3/00* (2006.01)
*A61B 5/00* (2006.01)
*A61B 5/044* (2006.01)
*G16H 40/63* (2018.01)
*G06F 3/0488* (2013.01)

(52) U.S. Cl.
CPC ........ *G06F 3/0488* (2013.01); *G06T 2200/04* (2013.01); *G06T 2207/30016* (2013.01)

(58) Field of Classification Search
CPC .... A61B 5/4887; G09G 3/002; G06F 3/0488; G06F 2203/04806; G06F 3/04842
See application file for complete search history.

(56) References Cited

U.S. PATENT DOCUMENTS

| | | | |
|---|---|---|---|
| 2007/0258620 A1 | 11/2007 | Nadar et al. | |
| 2008/0157764 A1* | 7/2008 | Kabasawa | G01R 33/56341 324/309 |
| 2008/0174311 A1 | 7/2008 | McGraw | |
| 2008/0205733 A1* | 8/2008 | Laidlaw | A61B 5/055 382/131 |
| 2015/0145857 A1* | 5/2015 | Whited | G06F 3/04845 345/419 |
| 2015/0363951 A1* | 12/2015 | Wedeen | A61B 5/055 345/419 |

* cited by examiner

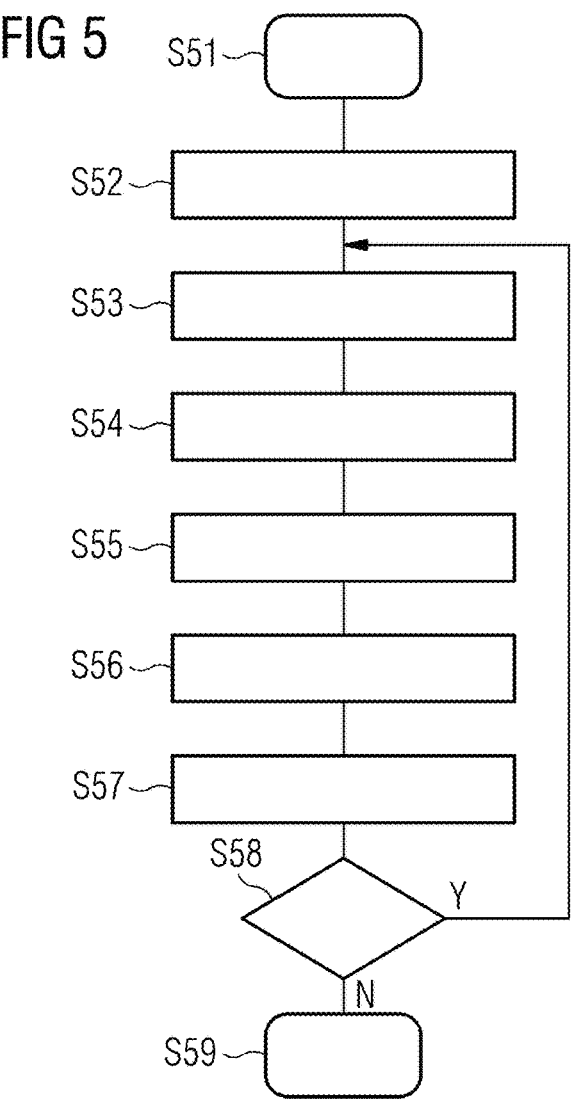
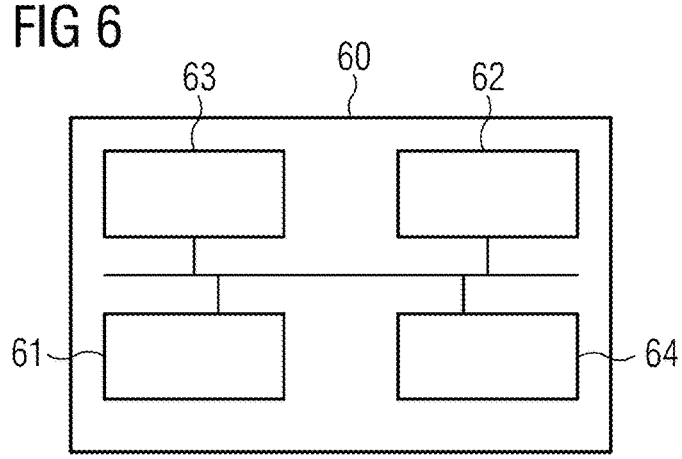

METHOD AND COMPUTER FOR VISUALIZATION OF FIBERS IN MEDICAL IMAGES

BACKGROUND OF THE INVENTION

Field of the Invention

The present application concerns a method for the combined visualization of information in an object under examination. The invention furthermore concerns a computer and a non-transitory, computer-readable data storage medium encoded with programming instructions that implements such a method.

Description of the Prior Art

It is known to acquire image data from examination subject as three-dimensional volume datasets, generated with imaging devices and MR systems or CT systems, etc. In each three-dimensional dataset, each pixel or voxel has a value that can be depicted encoded as a grayscale value or a color value, that is shown in the display of the dataset, for example as a two-dimensional slice in the three-dimensional dataset. The location of the two-dimensional slice can be on the main axes of the 3D dataset, i.e., transverse, sagittal, or coronal. Oblique orientation, or any free orientation in the three-dimensional dataset, is also possible.

A three-dimensional dataset can contain not only scalar values, but also vector data. One example of this is diffusion tensor data in which each voxel has a tensor. These three-dimensional datasets with vector information can furthermore be used to combine directional information in at least some of the voxels into fibers. These fibers then indicate the course of the directional information and, when applied in the brain, can represent the connection paths in the white brain matter or, when applied in the heart, the muscle connections of the heart. The number of fibers in an examination volume can be very high, for example millions of fibers in each dataset. For the depiction, it is possible to combine some fibers into fiber bundles so that the fiber bundles are then depicted, and this simplifies visualization in the display. These fiber bundles are generally depicted in addition to the anatomical information. A user wishing to depict the bundles and the associated anatomical information in order to visualize in the display, individual fibers or fiber bundles for the evaluation of these datasets will find such tracking difficult since the fibers are a curved object in the three-dimensional space and the user wants to know what anatomical information surrounds a bundle. For this purpose, the user must manually arrange the slice planes correctly in order to be able to identify the anatomy surrounding a fiber in the display.

U.S. Pat. No. 7,889,899 B2 describes a method for depicting diffusion tensor data by the use of a spherical scatter plot. U.S. Pat. No. 7,602,180 B2 describes a method for the two-dimensional depiction of three-dimensional diffusion tensor data.

SUMMARY OF THE INVENTION

An object of the present invention is to provide a method with which a fiber can be tracked in a simple manner with the surrounding anatomical information being depicted at the same time.

According to a first aspect of the invention, in a method for the combined visualization of image information in an examination subject at a display screen of a computer, the computer is provided with a first three-dimensional dataset of the examination subject in which anatomical information of the examination subject is shown. The computer is also provided with a second three-dimensional dataset in which the voxels contain directional information. In the second image dataset some voxels are combined along the respective directional information into a number of fibers. In the inventive method, a first viewing position in the examination subject is determined by the computer relative to a fiber selected from the multiple fibers. From the first three-dimensional dataset, a first item of anatomical information that is visible from the first viewing position. Then, the determined first item of anatomical information is projected by the computer onto a first projection surface in the display as a function of the first viewing position determined. If now a movement away from the first viewing position is detected, for example by actuation of an input element by a user that produces an input into the computer that designates the movement away from the first viewing position, a guided movement along the selected fiber is determined in the computer as a function of the detected movement. The guided movement is restricted to a movement along one of the multiple fibers. A second viewing position in the examination subject relative to the selected fiber is determined by the computer as a function of the guided movement, and a second item of anatomical information that is visible from the second viewing position is determined from the first three-dimensional dataset, and the second item of anatomical information is projected onto a second projection surface in the display.

As a result of the above-described method, upon a movement away from the first viewing position, there is automatically a movement along one of the fibers, so that the movement is converted into a guided movement along a fiber. In addition, the anatomical information for the first viewing position and the second viewing position is automatically calculated in each case, so that there is no need for a time-consuming and complicated manual adaptation of the movement to the fiber orientation and the selection of the projection surfaces.

For example, the movement away from the first viewing position can result from an interaction of a user with an input unit, wherein as a function of the interaction, a virtual observer is moved from the first viewing position along the selected fiber to the second viewing position. It is thus possible to determine a position relative to the selected fiber and a viewing direction relative to the selected fiber for both the first and second viewing position. Hence, it is possible for the location and the viewing direction relative to the fiber to be determined for the virtual observer moving along the selected fiber.

Thus, it is possible to use a specific default setting for the location and search direction, wherein this default setting can then be changed by a user input.

The projection surface is preferably calculated by the computer as a function of the viewing position in the examination subject, with at least the first projection surface being calculated at the first viewing position and the second projection surface at the second viewing position. This means that the projection surfaces change as a function of the viewing position and move together with the viewing position. It is also possible for projection surfaces to be calculated for each position between the first viewing position and the second viewing position, for the projection of the respective anatomy onto the projection surface. However, in order to reduce the amount of computing effort, it is also possible to calculate only the projection surface for the starting position, the first position, and for the end position, the second viewing position.

The projection surfaces can have a projection plane onto which the anatomical information is projected in each case. This projection plane is then determined at least for the first and the second viewing position. However, it is also possible for more projection surfaces to be calculated, such as two or three projection planes or surfaces, or one single surface onto which the accumulated anatomical information visible from the respective viewing position is then projected. When projection planes are used, it is possible for the first projection plane to be determined perpendicular to the direction of the selected fiber, wherein the second projection plane is determined such that it extends perpendicular to the first position plane. For the determination of the precise locations of the second projection plane, it is furthermore possible to take account of the location of a main axis of the second three-dimensional dataset, the location of an anatomical axis in the second three-dimensional dataset or the curvature of the selected fiber. The location of the first projection plane does not yet completely define the location of the second projection plane if it is assumed that the two projection planes should be perpendicular to one another. The aforementioned points can then be used to define the location of the second projection plane relative to the first projection plane.

However, the invention is not restricted to two or more projection planes that are perpendicular to one another. It is possible to use any other type of projection surface, such as a cylinder surrounding the fiber onto which the anatomical information surrounding the fiber is then projected.

It is also possible to determine further parameters for the projection surfaces such as a transparency value that indicates which of the items of anatomical information that lies behind the respective projection from the respective viewing position is visible from the first or second viewing position. The determined or calculated projection surfaces, such as the projection planes, can be completely non-transparent so that no anatomical information is depicted behind them. It is also possible for the respective projection surface to be semi-transparent so that anatomical information behind the projection surface is still partially depicted.

A voxel can contain more than A single item of directional information; more than one fiber can pass through a voxel. When a movement away from the first viewing position is detected, in the case of voxels with multiple fibers, the fiber can be selected that is nearest in the direction in which the movement away from the first viewing direction took place. If the directional information in the voxel has a main direction and at least one secondary direction, the fiber can be tracked along that main direction.

The invention furthermore encompasses a computer that implements the above-described method, the computer having a processor and a memory, wherein the memory stores control information (code) that can be executed by the processor so as to execute the above-described method.

The present invention also encompasses a non-transitory, computer-readable data storage medium encoded with programming instructions that, when the storage medium is loaded into a computer, cause the computer to implement any or all of the embodiments of the method according to the invention, as described above.

BRIEF DESCRIPTION OF THE DRAWINGS

FIG. 5 is a flowchart of a further embodiment of the invention, in which planes are used as projection surfaces.

FIG. 6 is a block diagram of a computer with which the method steps depicted in FIGS. 4 and 5 can be executed.

DESCRIPTION OF THE PREFERRED EMBODIMENTS

Figure 1:
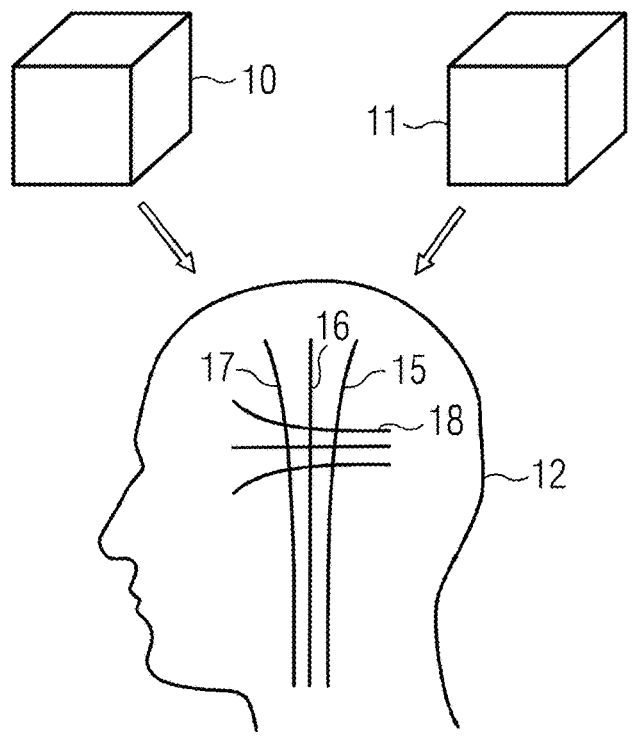
FIG. 1 schematically shows an examination subject with a combined depiction of the anatomical information and the directional information.

The following explains the present invention in more detail with reference to preferred embodiments and with reference to the attached drawings. In the figures, the same reference characters indicate the same or similar elements. The figures are schematic depictions of different embodiments of the invention. Herein, the elements depicted in the figures are not necessarily depicted true to scale and the elements depicted are reproduced in such a way that their functions and purpose become comprehensible for the person skilled in the art. Any connections between functional units or other elements shown in the figures can also be implemented from indirect connections, wherein a connection may be implemented in a wired or wireless manner. Functional units may be implemented as hardware, software or a combination of hardware and software.

FIG. 1 schematically shows a first three-dimensional dataset 10 substantially containing anatomical information, and a second three-dimensional dataset 11 substantially containing directional information. The datasets 10 and 11 can, for example, be MR datasets, wherein the directional information contained in the voxels of the dataset 11 can, for example, be a diffusion direction or a diffusion tensor. Hence, one item of directional information or several items of directional information can be present for each voxel. These two datasets can be combined as shown at the bottom of FIG. 1 in order to depict an object under examination 12, wherein, in addition to the anatomical information depicted, various other fibers 15, 16, 17 or 18 are also depicted. The fibers can be individual fibers or fiber bundles, wherein a fiber is defined as a string of directional information in the individual voxels. Hence, the fiber is a combination or string of directional information present in a voxel. In the case of a tensor, the directional information can include a main direction and one or more secondary directions. A voxel can contain a fiber for every main direction and for some or all of the secondary directions so that a voxel can also contain multiple fibers.

The following describes the method according to the invention and how it makes possible, in a simple way, tracking individual fiber orientations while at the same time depicting the anatomical information as a function of the selected position on one of the fibers. For this purpose, a starting or first viewing position along one of the fibers is determined in the combined dataset with the anatomical information and the directional information. This is, for example, possible by the selection of one of the fibers and a point on a fiber by a user.

Figure 2:
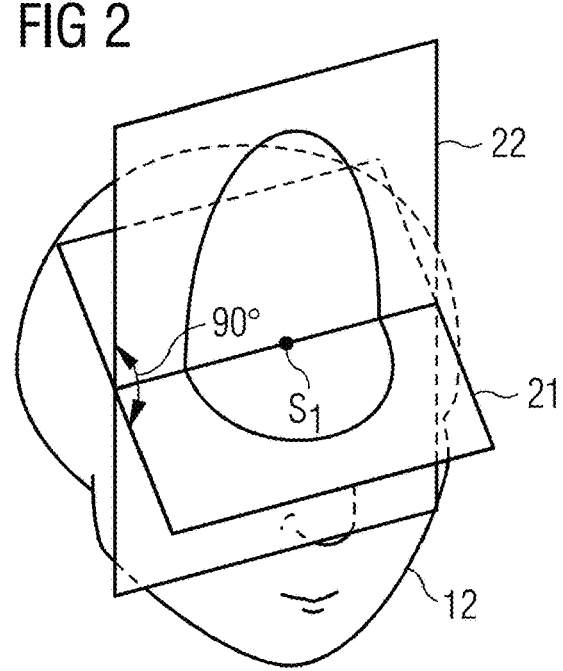
FIG. 2 schematically shows, in the case of movement along a fiber, the anatomical information is projected onto projection surfaces.

Depending upon the first viewing position relative to the selected fiber, it is now possible to determine the first item of anatomical information visible from the first viewing position from the first 3D dataset. This is depicted schematically in FIG. 2, wherein the object under examination is a brain. Herein, the anatomical information visible from a first viewing position S1 is projected onto two projection surfaces, namely the projection plane 21 and the projection plane 22, which are perpendicular to one another. The information on the sectional view/projection planes typically corresponds to the grayscale value for the anatomical information (3D dataset), which is intersected at the points of the projection plane. This can be simple grayscale values from a for example T1-weighted image, or (semi-)quantitative values (for example ADC, T1, etc.) or for example encoded values for a segmentation of brain structures. The shape of the "projection surfaces" is optional, i.e. one or more planes, other shapes, such as a cylinder, a paraboloid, etc. with settings that are configurable for each pixel, such as transparency. Also possible is restriction to a specific distance range from the fiber, i.e. a circle or an ellipse.

Figure 3:
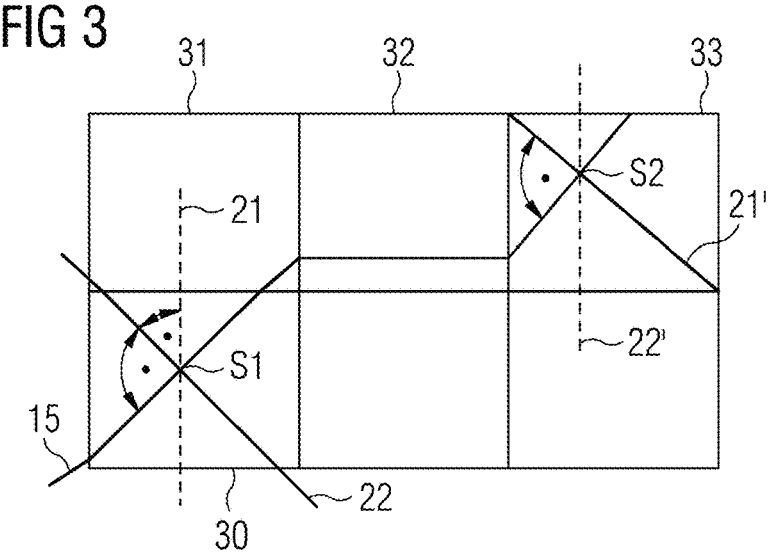
FIG. 3 schematically shows, in the case of directional information in different voxels, in each case two slice planes serving as projection surfaces for the projection of the anatomical information are calculated for two viewing positions.

FIG. 3 is a schematic depiction of a fiber 15 showing how it extends in the individual voxels 30, 31, 32 and 33. In the example shown, it is assumed that the first viewing position is at the point S1. For this viewing position, it is then possible to calculate a plane 22 perpendicular to the fiber direction. It is also possible for a second plane 21 to be calculated, which is in turn perpendicular to the plane 22. For the complete definition of the plane 21, it is furthermore possible to determine the angle of rotation of the two planes relative to one another, which is, for example, dependent upon the main axis of the 3D volume or the anatomical axis of the object depicted or is determined as a function of a defined center of gravity or as a function of the local curvature of the fiber. If a movement by the user or the person is detected, such as the detection of a mouse movement or a rotary control, detection of a position on a touch-sensitive screen, detection of a gesture or detection of a control command, this movement is converted into a movement along the selected fiber. The distance by which the viewing position hereby moves from the first viewing position S1 to the second viewing position S2, can hereby depend upon the detected movement, for example upon the intensity or length of the interaction. Then, at the viewing point S2, in turn a projection planes 22' and a projection plane 21' are calculated according to the same criteria as for the calculation of planes 21 and 22. The anatomical information visible from the viewing position S2 is then projected onto the two planes 21' and 22'. If a voxel contains more than one item of directional information, depending upon the detected movement, the movement can be converted into a guided movement along the fiber that corresponds most closely to the detected movement. For example, if a fiber in the adjacent voxel branches to a fiber extending toward the left or right or a fiber extending upward or downward, the selected direction can be tracked as a function of the detected movement.

Figure 4:
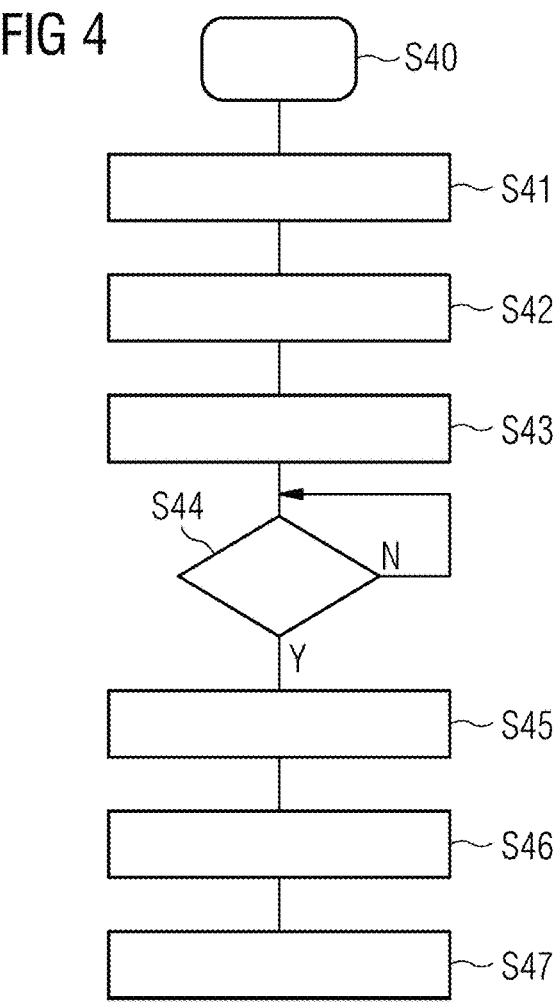
FIG. 4 is a flowchart with the basic steps performed in the method for the combined visualization of information according to the invention.

FIG. 4 summarizes some essential steps of the method. The method starts in the step S40 and a first viewing position in the object under examination relative to one selected fiber is determined in a step S41. Then, a first item of anatomical information that is visible from the first viewing position is determined in a step S42 and, in a step S43, this item of anatomical information is finally projected onto the first projection surface, wherein the projection surfaces can be determined as described in FIG. 3. Obviously, the projection surfaces are not restricted to projection planes. Other projection surfaces such as, for example, cylindrical projection surfaces surrounding the fiber or spherical projection surfaces surrounding the viewing position are conceivable. In a step S44, a check is performed as to whether a movement is detected, for example due to actuation of a control element. If this is the case, the detected movement is converted into a guided movement along one of the fibers in a step S45. In a step S46, a second viewing position relative to the selected fiber is determined as a function of the guided movement, and, in a step S47, the second item of anatomical information that is visible from the second viewing position is determined and projected onto the second projection surface.

FIG. 5 shows a further embodiment of the method for the determination of the combined visualization of the anatomical information and the directional information. The method starts in the step S51 and, in a step S52, the fiber or the fiber bundle on which the first viewing position is to lie is selected. Then, in a step S52, the first viewing position on the fiber is defined. Herein, the virtual observer position or viewing position can be defined such that the location relative to the fiber and the viewing direction relative to the fiber is defined. Herein, the viewing position can be directly on the fiber or at a certain distance relative to the fiber, wherein the viewing direction can be oriented along the fiber or on a specific point relative to the fiber (step S53). Then, in the step S54, the projection surface for the first viewing position is determined, for example the location of a plane E1 relative to the fiber, for example a plane extending perpendicular to the fiber in the respective voxel. Then, in a step S55, a second projection plane can be determined, which, for example, extends perpendicular to the first projection plane and is selected as a function of further information such as the anatomical axis of the object under examination or the main axis of the 3D volume etc. With knowledge of the projection planes 21 and 22, in step S56, a third projection plane can be calculated, wherein in this case, three projection planes are used for the projection of the anatomical information. Finally, in a step S57, the calculated planes can be depicted, wherein additional attributes such as the transparency of individual planes have been determined. In a step S58, a check is performed as to whether a movement of the first viewing position away from the first viewing position is detected. If this is the case, the steps of the determination of the viewing position to the depiction of the determined projection planes are repeated until there is no further movement and the method ends in a step S59.

With the above-described method, it is possible to effect a rotation of the 3D volume automatically, for example as a function of the relative viewing position and the angle to a target point; for example, the viewing direction can be selected along the fiber or a viewing direction perpendicular to one of the planes.

In the example shown in FIG. 5, three slice planes were calculated. Obviously, the projection can also be onto two planes or more than three planes. It is furthermore possible to adapt the rotation of the slices with the aid of a further input by an operator. Similarly, the individual projection planes do not have to be perpendicular to one another, other relative orientations to one another or to the selected fiber are also possible. In the case of three-dimensional data with directional information, the directional information can be based on diffusion directions, but other blood flow directions are also conceivable. The viewing direction and viewing position relative to a selected fiber can also be changed by an input and do not have to be fixed.

FIG. 6 is a block diagram of a computer 60 for combined visualization with which the above-described method steps can be carried out. The computer 60 has an input unit 61 via which an operator can select a starting position on a fiber, and possibly a location relative to the fiber and a viewing angle relative to the fiber. The input unit 61 is also provided to move the virtual user from the first viewing position to the second viewing position.

The computer 60 can also have further interfaces for communication with other units or for loading the datasets 10 and 11.

The computer 60 furthermore has a processor 62, which is responsible for the operation of the computer 60. The processor 62 has one or more processing circuits and can execute commands stored in a memory 63. The memory 63 can furthermore store the program code or program modules that can be executed by the processor 62 in order to carry out the above-described method or the above-described functions. The desired information can then be depicted on a display unit 64 as the combined dataset. The computer 60 can have further functional units, but these are not shown for clarity.

It is also conceivable for the determined visual information to be depicted not only on a screen, but also in 3D glasses. Instead of a set of projection planes, it is also possible to select other two-dimensional functions, such as a parabola, wherein the apex is in the viewing position.

The above-described method enables a simple depiction of anatomical information along the fibers. It is possible to dispense with laborious manual selection of the individual planes at the individual viewing positions and movement along one of the fibers is enabled by a simple movement.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for combined visualization of image information of an examination object at a display screen of a computer, said method comprising:
    providing said computer with a first 3D dataset comprising voxels that represent anatomical image information of the examination object, and with a second 3D dataset comprising voxels that each comprise at least one item of directional information;
    in said computer, combining at least some of the voxels in said first 3D dataset with at least some corresponding voxels in said second 3D dataset so as to produce a plurality of fibers;
    in said computer, determining a first viewing position of the examination object at said display screen, relative to a selected fiber that is selected from said plurality of fibers;
    in said computer, determining, from said first 3D dataset, a first item of anatomical image information that is visible from said first viewing position;
    in said computer, projecting said first item of anatomical image information onto a first projection surface at said display screen as a function of said first viewing position;
    in said computer, receiving a manual input that designates a movement away from said first viewing position and, in said computer, detecting said movement away from said first viewing position;
    in said computer, determining a guided movement of the selected fiber as a function of the detected movement, and restricting said guided movement to a movement along said selected fiber;
    in said computer, determining a second viewing position of the examination object relative to the selected fiber, as a function of the guided movement; and
    in said computer, determining, from said first 3D dataset, a second item of anatomical image information that is visible from the second viewing position, and projecting said second item of anatomical information onto a second projection surface at said display screen.

2. A method as claimed in claim 1 wherein said manual input designating said movement away from said first viewing position represents movement by a virtual observer from said first viewing position along said selected fiber to said second viewing position.

3. A method as claimed in claim 1 comprising determining each of said first and second viewing positions by determining a position relative to the selected fiber and determining a viewing direction relative to the selected fiber.

4. A method as claimed in claim 3 wherein each of said first and second projection surfaces has at least one projection plane onto which the respective first or second anatomical image information is projected, and determining said at least one projection plane in said computer for each of said first and second viewing positions.

5. A method as claimed in claim 4 wherein each of said first and second projection surfaces comprises two projection planes that are perpendicular to said selected fiber, and, in said computer, determining a second of said two projection planes by first determining a first of said two projection planes and then determining said second of said two projection planes to be perpendicular to said first of said two projection planes.

6. A method as claimed in claim 5 comprising, in said computer, calculating a location of said second of said two projection planes relative to said first of said two projection planes dependent on at least one of a main access of said second 3D dataset, a location of an anatomical axis in said second 3D dataset, and a curvature of the selected fiber.

7. A method as claimed in claim 1 comprising, in said computer, for each of said first and second projection surfaces, determining a transparency value that designates which of said items of anatomical image information, that are behind the respective first or second projection surface from the respective first or second viewing position, are visible from the respective first or second viewing position.

8. A method as claimed in claim 1 wherein at least some of the corresponding voxels in said second 3D dataset that are combined to produce said plurality of fibers have more than one item of directional information because a plurality of fibers pass therethrough.

9. A method as claimed in claim 8 comprising, in said computer, detecting said movement away from said first viewing position by selecting a fiber in said voxel that is nearest a direction in which said movement away from the first viewing position takes place.

10. A computer for combined visualization of image information of an examination object, said computer comprising:
    a processor;
    a display screen in communication with said processor;
    said processor being provided with a first 3D dataset comprising voxels that represent anatomical image information of the examination object, and with a second 3D dataset comprising voxels that each comprise at least one item of directional information;

said processor being configured to combine at least some of the voxels in said first 3D dataset with at least some corresponding voxels in said second 3D dataset so as to produce a plurality of fibers;

said processor being configured to determine a first viewing position of the examination object at said display screen, relative to a selected fiber that is selected from said plurality of fibers;

said processor being configured to determine, from said first 3D dataset, a first item of anatomical image information that is visible from said first viewing position;

said processor being configured to project said first item of anatomical image information onto a first projection surface at said display screen as a function of said first viewing position;

said processor being configured to receive a manual input that designates a movement away from said first viewing position and, in said processor, detecting said movement away from said first viewing position;

said processor being configured to determine a guided movement of the selected fiber as a function of the detected movement, and restricting said guided movement to a movement along said selected fiber;

said processor being configured to determine a second viewing position of the examination object relative to the selected fiber, as a function of the guided movement; and said processor being configured to determine, from said first 3D dataset, a second item of anatomical image information that is visible from the second viewing position, and to project said second item of anatomical information onto a second projection surface at said display screen.

11. A non-transitory, computer-readable data storage medium encoded with programming instructions, said storage medium being loaded into a computer that is in communication with a display screen, and said programming instructions causing said computer to:

receive a first 3D dataset comprising voxels that represent anatomical image information of the examination object, and with a second 3D dataset comprising voxels that each comprise at least one item of directional information;

combine at least some of the voxels in said first 3D dataset with at least some corresponding voxels in said second 3D dataset so as to produce a plurality of fibers;

determine a first viewing position of the examination object at said display screen, relative to a selected fiber that is selected from said plurality of fibers;

determine, from said first 3D dataset, a first item of anatomical image information that is visible from said first viewing position;

project said first item of anatomical image information onto a first projection surface at said display screen as a function of said first viewing position;

receive a manual input that designates a movement away from said first viewing position and, in said computer, detecting said movement away from said first viewing position;

determine a guided movement of the selected fiber as a function of the detected movement, and restricting said guided movement to a movement along said selected fiber;

determine a second viewing position of the examination object relative to the selected fiber, as a function of the guided movement; and determine, from said first 3D dataset, a second item of anatomical image information that is visible from the second viewing position, and project said second item of anatomical information onto a second projection surface at said display screen.

* * * * *